United States Patent [19]

Farrington et al.

[11] Patent Number: 4,915,897

[45] Date of Patent: Apr. 10, 1990

[54] TRANSVERSE POCKET FORMING MACHINE AND METHOD FOR USE THEREOF

[75] Inventors: Allan P. Farrington, Englishtown; Gerald M. Marshall, Somerville; Nicholas Wereson, Spotswood, all of N.J.

[73] Assignee: Chicopee, New Brunswick, N.J.

[21] Appl. No.: 298,860

[22] Filed: Jan. 20, 1989

Related U.S. Application Data

[63] Continuation of Ser. No. 99,874, Sep. 22, 1987, abandoned.

[51] Int. Cl.⁴ ............................................. D04H 1/72
[52] U.S. Cl. .................................. 264/517; 264/113; 264/116; 425/81.1; 425/82.1
[58] Field of Search ............. 264/517, 518, 121, 113, 264/116, 115; 425/80.1, 81.1, 82.1, 254

[56] References Cited

U.S. PATENT DOCUMENTS

| | | | |
|---|---|---|---|
| 1,695,327 | 12/1928 | Goldston | 425/254 |
| 2,054,001 | 9/1936 | Polak | 425/254 |
| 3,740,797 | 6/1973 | Farrington | 264/518 |
| 3,772,739 | 11/1973 | Lovgren | 425/82.1 |
| 3,857,657 | 12/1974 | Teed | 264/517 |
| 3,963,392 | 6/1976 | Goyal | 425/82.1 |
| 4,666,647 | 5/1987 | Enloe et al. | 264/121 |
| 4,701,294 | 10/1987 | Radwanski et al. | 264/518 |

*Primary Examiner*—Jan H. Silbaugh
*Assistant Examiner*—Mary Lynn Fertig
*Attorney, Agent, or Firm*—Joseph F. Shirtz

[57] ABSTRACT

A pad is formed by feeding separate supplies of fibrous material into contact with two separate lickerins that are parallel to each other and rotated toward each other. The fibers from the two lickerins pass through a mixing zone and are accumulated in pocket molds moving on a conveying screen that is moved parallel to the axes of the lickerins. A baffle plate may be inserted into the mixing zone and acts to control the lateral or cross-sectional composition of a web formed by the fibers accumulated in the molds. When different fibrous materials are fed to the lickerin along their length, the vertical composition of the web is altered. Because of the pocket molds the pads are formed as individually shaped products.

10 Claims, 4 Drawing Sheets

TRANSVERSE POCKET FORMING MACHINE AND METHOD FOR USE THEREOF

This is a continuation of application Ser. No. 99,874, filed Sept. 22, 1987, now abandoned.

TECHNICAL FIELD

This invention relates to an improved method and apparatus for molding composite nonwoven web products of various shapes and sizes consisting of a more or less uniform intermixture of randomly oriented fibers and/or particulate matter obtained from separate supplies of individualized source material such as textile fibers, paper-making fibers and powders.

BACKGROUND OF THE INVENTION

Nonwoven fiber webs or structures frequently consist of a random yet homogeneous agglomeration of long and short fibers. Long fibers are fibers of both natural and synthetic origin that are suitable for textiles. They are longer than 0.25 inches and generally range between 0.5 and 2.5 inches in length. Short fibers are suitable for paper-making and are generally less than about 0.25 inches long, such as wood pulp fibers or cotton linters.

Nonwoven web products may also comprise particulate matter, such as absorbent powders, in combination with long and short fibers. For example, a highly absorbent powder or fiber can be held within a pocket of fibers having good water moving properties.

There are many different methods and devices useful for making nonwoven webs or structures. Conventional carding or garnetting methods produce nonwoven fiber webs, but these are generally limited to textile length fibers. Methods of forming nonwoven web products in pockets, i.e., having a non-uniform cross section, a predetermined topography, or sharply defined edges are also known.

The "Rando-Webber" process may be used to make nonwoven webs. In this process, pre-opened textile fiber material is delivered to a lickerin that opens the fibers further, and introduces them to a high-velocity low-pressure air stream. The fibers are randomly deposited on a condensing screen to form an isotropic web. While a uniform web of textile fibers can be obtained, this process is not suitable for use with short fibers or blends of long and short fibers.

U.S. Pat. No. 3,512,218 of Langdon describes two lickerins and rotary feed condenser assemblies arranged in parallel one after the other. Isotropic nonwoven webs are formed with this apparatus by feeding fibers deposited on a condenser mat to the lickerins, where the fibers are individualized. A single airstream is divided into two parts and acts to doff the fibers from the lickerins and deposit them onto a suction box, where the web is formed. This method cannot be used to homogeneously blend two streams of fibers.

In U.S. Pat. No. 3,535,187 of Wood there is described apparatus for producing a layered web of randomly oriented fibers joined at the interface of adjacent layers by a small zone of textile length fibers extending across the interface. Wood's device provides individualized fibers which are deposited on a pair of cylindrical condenser screens by a pair of respective lickerins acting in cooperation with high speed turbulent air streams that move faster than the lickerin in order to doff the fibers. However, the air speed must also be controlled so that the fibers do not forcibly impact on the condensers. The condenser screens are positioned closely adjacent to one another and the layers of fibers on the condensers are compressed between the condensers to form a composite nonwoven web with some blending at the interface between layers. As a result, there is no substantial fiber mixing zone adjacent to the condensers, and the intermixing of fibers is minimal.

One way of making a nonwoven web consisting of a mixture of randomly oriented long and short fibers uses a milling device to individualize short fibers and a lickerin to individualize long fibers. The fibers are mixed in a mixing zone, and the mixture is deposited on a condenser to form a nonwoven web. Though randomly oriented, the mixed fibers are stratified rather than homogeneously blended. The long fibers predominate on one side of the web and the short fibers predominate on the other. In addition, undesirable clumps of fibers or "salt" occur in this web product, because the mill does not completely individualize the short wood pulp fibers.

Another method used to make webs of mixed and randomly oriented long and short fibers introduces pre-opened long and short fibers to a single lickerin for individualization. However, the optimum lickerin speeds for long and short fibers are different. To prevent the degradation of long fibers, this device must operate at the slower speed that is optimum for long fibers. As a result, the speed and throughput of the device is compromised.

Methods and devices which produce a blend of long and short fibers without clumps or salt are disclosed in U.S. Pat. No. 3,772,739 of Lovgren. Lovgren provides for the separate and simultaneous individualization of each type of fiber on separate lickerins, each operating at an optimum speed for the fiber it opens. For example, long fibers such as rayon are supplied to a lickerin operating in the neighborhood of 2400 rpm. Pulpboard is supplied to a lickerin operating in the neighborhood of 6000 rpm, a speed that would damage long fibers. The fibers are doffed from their respective lickerins by separate air streams and are entrained in the separate air streams. These streams are subsequently mixed in a mixing zone in order to blend the fibers. The homogeneous blend is then deposited in a random fashion on a condenser disposed in proximity to the mixing zone. While the Lovgren apparatus is useful, it does not lend itself to the preparation of a wide variety of webs.

Another method of producing homogeneous blends of 5 fibers is disclosed in commonly owned U.S. Pat. No. 3,740,797 of Farrington. Farrington discloses a method and machine wherein supplies of fibers are fed to oppositely rotating parallel lickerins, which are operated at respective optimum speeds to produce individualized long and short fibers. The individualized fibers are doffed from the lickerins by centrifugal force and by high velocity air streams directed against any fibers tending to cling to the lickerin structure. The individualized fibers from each supply are entrained in their respective air streams and are impelled toward each other at high velocities along trajectories that terminate in a mixing zone, where at least a portion of the fibers from each supply may be blended. A suction actuated condensing means communicates with the mixing zone so that the blended fibers are deposited on a condenser screen to produce an isotropic web of fibers. This screen is moved in a direction, i.e. the "machine direction," which is perpendicular to the axis of the lickerins. In addition, a baffle can be interposed between the air streams to control the degree of mixing and the respective location of the long and short fibers in the composite web.

It would also be advantageous to provide composite web structures having a non-uniform cross section or predetermined topography comprising zones of different fiber or particulate materials and blends thereof. For example, a method and apparatus for making nonwoven structures having selectively absorbent properties along the product's cross-section is desirable, as in the case of hygiene products such as sanitary napkins. It is particularly desirable to provide for blended composite structures having predetermined shapes with sharply defined edges.

Methods and machines for making nonwoven fluff pulp pads and pre-shaped absorbent products are known, but do not provide for selective blending and layering of pulp, textile, and particulate materials. Conventional pocket-forming devices can process only one material, usually pulp, and cannot be readily modified to provide uniformly blended pads because of the complex geometry inherent in the use of hammer mills or disc mills and cylindrical product-forming surfaces. Typical of these conventional devices are machines available from Winkler & Dunnebier Maschenfabrik and Curt G. Joa, Inc. See, for example, U.S. Pat. Nos. 4,560,379 and 4,598,441 of Stemmler. [owned by W&D]. PCT Application No. WO 85/04366 of Johnson et al. is also of interest. Johnson teaches the use of fiber-receiving molds disposed on a continuously rotating drum selectively provided with a vacuum. Other foraminous drum arrangements having circumferential cavities are taught by U.S. Pat. No. 4,592,708 of Feist et al. and U.S. Pat. No. 3,518,726 of Banks.

An early method of making sanitary napkins is disclosed in U.S. Pat. No. 2,073,329 of Winter. Winter teaches that patches of loose cotton fibers may be blown down onto a gauze-like material at regular intervals in cooperation with a suction means. Then pads of absorbent material may be placed over the cotton patches, and the gauze folded and cut at regular intervals to make the napkins. The loose cotton fibers are directed to the surface of a moving wheel having spaced and screened suction inlets adapted to receive and condense the cotton fibers in uniform patches. The Winter process requires several time-consuming and independent steps, followed by the assembly of the composite structure from its component structures. It does not provide for a composite shaped and layered structure formed by blending one or more fibrous and/or particulate materials in an integral operation.

U.S. Pat. No. 2,949,646 of Clark is also representative of the prior art, and sets forth the problem of providing three-dimensionally shaped structures having sharply defined edges. Clark recites a prior art method wherein fibers are deposited continuously from an entraining air stream onto a continuously moving foraminous belt provided with suction. The belt is partially masked in order to provide deposition and condensation of fibers into a web having the desired shape. Clark notes that this method is disfavored because of the leakage of fibers from the masked to the unmasked regions of the belt, resulting in non-uniform layers. The prior use of pans to catch fibers deposited by gravity is mentioned by Clark, as is a method of cutting webs to desired shapes, or separating webs using caul plates.

The improvement of the Clark invention over the prior art is a fiber depositing head whereby unblended web structures having contoured edges are made by entraining previously individualized fibers in a circular path within a circular housing, delivering uniform volumes of entrained fibers to a moving collecting wall through openings in a foraminous separating wall of the housing, and forming a continuous web from the delivered fibers over collecting or masking members on the collecting wall. A clean separation of the continuous web into individual mats is achieved by a trough arrangement on the collecting wall, which trough separates adjacent collecting members and prevents leakage of fibers onto the collecting members by trapping excess fibers. A means for separating the masked collecting members from the end-product is also described.

A number of absorbent articles, and methods and machines for making them, are disclosed in the patents of Kolbach, U.S. Pat. Nos. 3,846,871; 3,860,002; 3,973,291; and 4,016,628. The '002 and '628 patents relate to adhesively bonded composite structures having a medial portion of greater basis weight than flanking end and side portions. These structures are obtained by providing discrete zones of relatively high and low suction on a foraminous forming surface.

The '871 and '291 patents describe a moving pad forming assembly having spaced, three-dimensional fiber-receiving compartments separated by air-impermeable regions. Each compartment has the shape of the desired end-product and is provided with a foraminous lower surface and movable air-impermeable side walls. Individualized fibers are provided to the compartments, which in turn communicate with a fiber-entraining suction means. Selective masking of the suction means can be used to influence the density and weight of material collected within regions of each compartment, and different air-suspended fibers are deposited to different compartment sections at different, non-overlapping, times to achieve different weight and density zones within each compartment.

U.S. Pat. Nos. 3,939,240 and 4,005,957 to Savich disclose a method and an apparatus for forming fibrous pads. Savich teaches a continuously driven condenser roll having three-dimensional foraminous cavities about its periphery. Each cavity is provided with a vacuum and is brought into communication with a pad forming region that is supplied with air-suspended fibers. The fibers are deposited within the cavity and form a layer, after which each layer is removed from its cavity as a pad by another vacuum cooperating with a proximate downstream transfer conveyor. The opening into each cavity has a smaller surface area than the surface area within the cavity, so that the resulting pads are consolidated within the cavity, resulting in an increased basis weight, rather than an advantageously shaped and sharply defined composite web structure.

The prior art does not provide discrete composite nonwoven structures having predetermined shapes and consisting of layers and/or vertical zones comprising blends of long fibers, short fibers and/or particulate matter. A method and apparatus capable of providing these structures is unknown, and in particular the prior art methods do not teach a means of producing such structures in a single continuous operation.

SUMMARY OF THE INVENTION

The present invention is directed to the high-speed production of blends of long and short fibers, with or without particulate matter, that result in a wide variety of composite nonwoven web structures of different widths, thickness, discrete shapes and compositions.

In an illustrative embodiment of the invention two independent fiber sources driven by feed rolls are individualized by parallel counter-rotating lickerins. The individualized fibers are doffed from the lickerins by air streams and centrifugal force, and are carried to a mixing zone. The fibers may be randomly and uniformly mixed, or kept in separate streams, and are deposited onto a condensing screen in a condensing zone located below the parallel lickerins and defined generally by the space between them. The screen supports and moves a series of product molds or pockets with open tops and bottoms in a direction generally parallel to the axes of the lickerins so that the lickerins deposit material in the pockets. The fibers fill the pockets and are thus molded into shapes defined by the shapes of the pockets.

Duct plates may be used to additionally define a path between the lickerins and the top surface of the pockets, and a suction slot under the screen may be preferably used to help deposit the fibers into the pockets and onto the screen. Since the screen travels parallel to the lickerin axes, there is a high-speed transverse formation of a series of shaped structures. The transverse webber according to the invention provides a relatively long web formation zone that is limited only by the practical length of the lickerins, the practical angle of divergence of the duct plates, and the practical length of the duct plates from the mixing to the condensing zone.

Composite and layered structures can be made by varying the material introduced to the lickerins along the length of each lickerin. Webs having different cross-sectional shapes can be generated by varying the configuration of the duct plates or the screen slot, by introducing baffles, or by programmably driving the feed rolls.

Separate sources of short and long fibers, such as pulp and rayon, respectively, are individualized by separate lickerins and formed into a structure. Each fiber source is guided by feed rolls and a nose bar into engagement with its lickerin, and each lickerin is rotated at a high speed that is suitable for the fibers it is acting on. The two lickerins are parallel to each other and rotate toward each other, i.e. in opposite directions. The nose bar and lickerin are arranged to provide the optimum opening relationship for the fibers. Each lickerin acts on its fiber supply and rapidly individualizes the fibers through violent contact between the fiber supply and the rapidly rotating teeth of the lickerin.

The streams of individual fibers are directed downward and toward each other so they meet in a mixing zone. However, the streams of fibers entering the mixing zone are dilute, allowing the two streams to intersect each other without a substantial number of collisions. As a result the fibers from the lickerin to the left of the condenser screen carrying the molds tend to reach predominately the right side of the screen and visa versa. The deposition of fibers occurs as the condenser screen with the molds moves along the length of the lickerins, e.g. 40 inches.

A different mixing pattern of the fibers can be accomplished by inserting a baffle into the mixing zone between the lickerins. This baffle intersects part of each stream of fibers and deflects it back in the opposite direction such that the long and short fibers are spread across the lateral width of the web. This results in a proportionally uniform mixing of the long and short fibers across the web. If the baffle completely intersects the streams, the material from the lickerin on the left is reflected back to the left and vise versa, so that a product with a distribution essentially opposite that with no baffle is created.

The pockets determine the shape of the formed structure; but, the thickness and density of the web is determined primarily by the fibers chosen, the proportion at which they are mixed, the feed roller speed, and the rate at which the condensing screen moves the pockets.

Different composition pulp and textile fibers can be fed simultaneously to their respective lickerins in a side-by-side relationship. In one such embodiment, pulp and textile fibers are fed into the device from the rear (i.e., toward the entrance for the pocket molds into the frame) to form a bottom layer of the structure, while another material is fed toward the front (i.e., the exit for the pockets) to form a top layer. These vertical zones can be varied by feeding different materials along the lickerin length in cooperation with one or more baffles.

In this way, different mixing zones can be defined, and the resulting structure can be formed with horizontal and vertical layers or zones. Each web zone is integrally associated with its adjacent web zone or zones by entangling of fibers across the interface; and each zone has a different but uniform composition of randomly oriented fibers.

The molds or pockets according to the present invention conform to the desired product shape and are directed through the condensing zone on a conveying screen. A suction means, and a cover assembly adapted to prevent undesirable leakage of air streams or loss of suction pressure are also provided in the condensing zone.

Alternatively, the conveyor screen may be eliminated and the molds may incorporate an integral condensing screen. In such a case the molds may be fed serially to the condensing zone disposed beneath the mixing zone of the webber by means of belts, chains, etc. In either case, within the condensing zone, the molds mate with each other and with a sealing assembly, provided for example by the ducts, so that all of the fibers are condensed onto either the mold screens or the conveyor screen, thereby forming individual shaped pads of fibrous material.

The pocket-forming condensing means is interchangeable with a continuous web condensing screen comprising a foraminous conveyor belt, provided that in all cases the direction of motion of the condensing screen is parallel to the lickerin axes. Although a pocket-forming condensing means can be used with a conventional double-lickerin webber, such a method and apparatus is limited to two materials and therefore cannot produce horizontal layers and vertical zones within the molds. Production capacity in a conventional webber can only be increased by increasing the lickerin length and forming pockets in parallel, resulting in a very complex machine. By using a transverse webber, capacity can be increased by increasing the lickerin length and the linear speed of the pockets or molds.

BRIEF DESCRIPTION OF THE DRAWINGS

The foregoing advantages and numerous other features of the invention will be more readily understood and appreciated in light of the following detailed description and accompanying drawings, wherein.

DESCRIPTION OF ILLUSTRATIVE EMBODIMENTS

Figure 1:
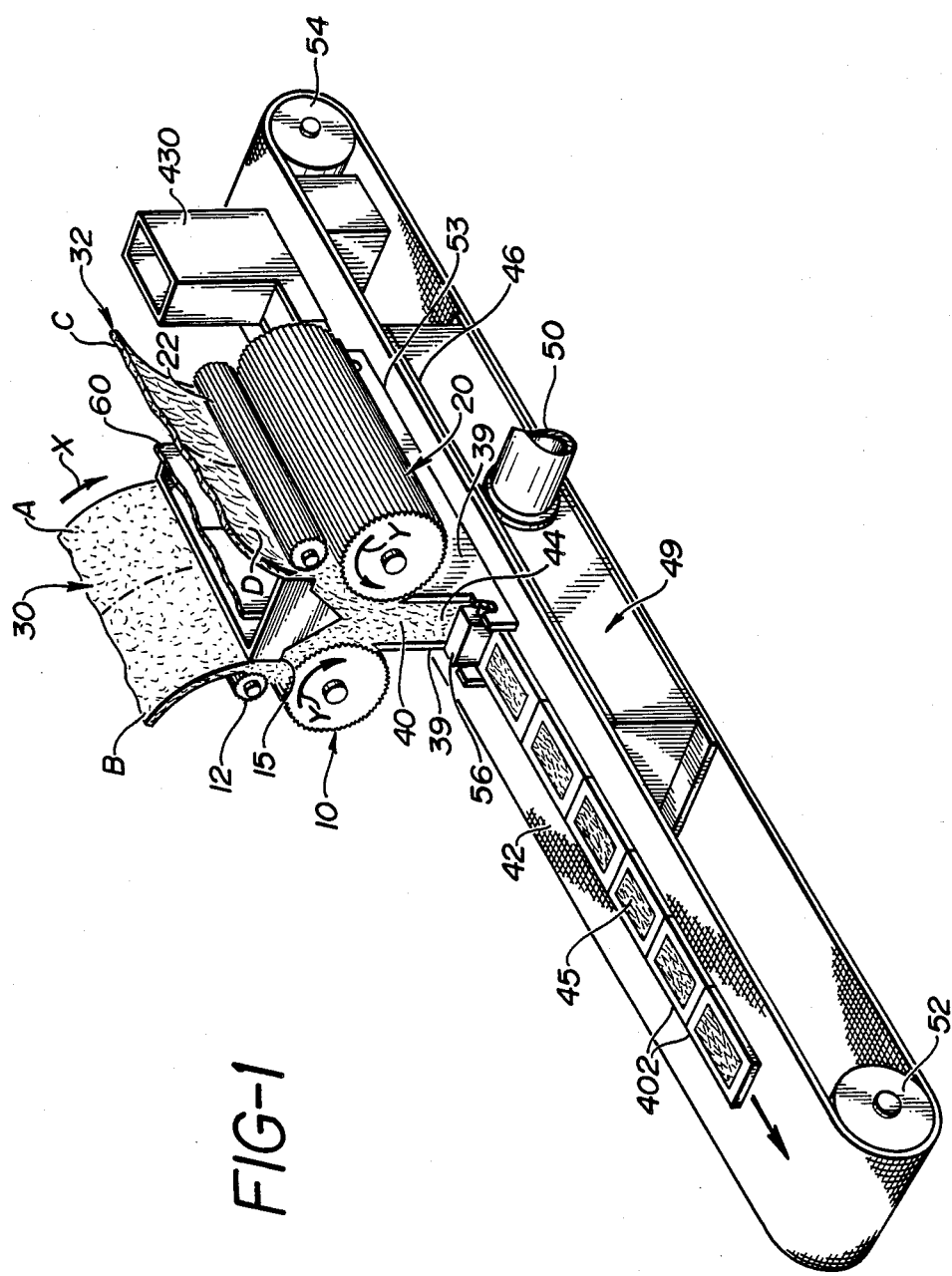
FIG. 1 is a schematic view of a transverse webber equipped with pocket molds according to the invention, showing the main components thereof.
Figure 2:
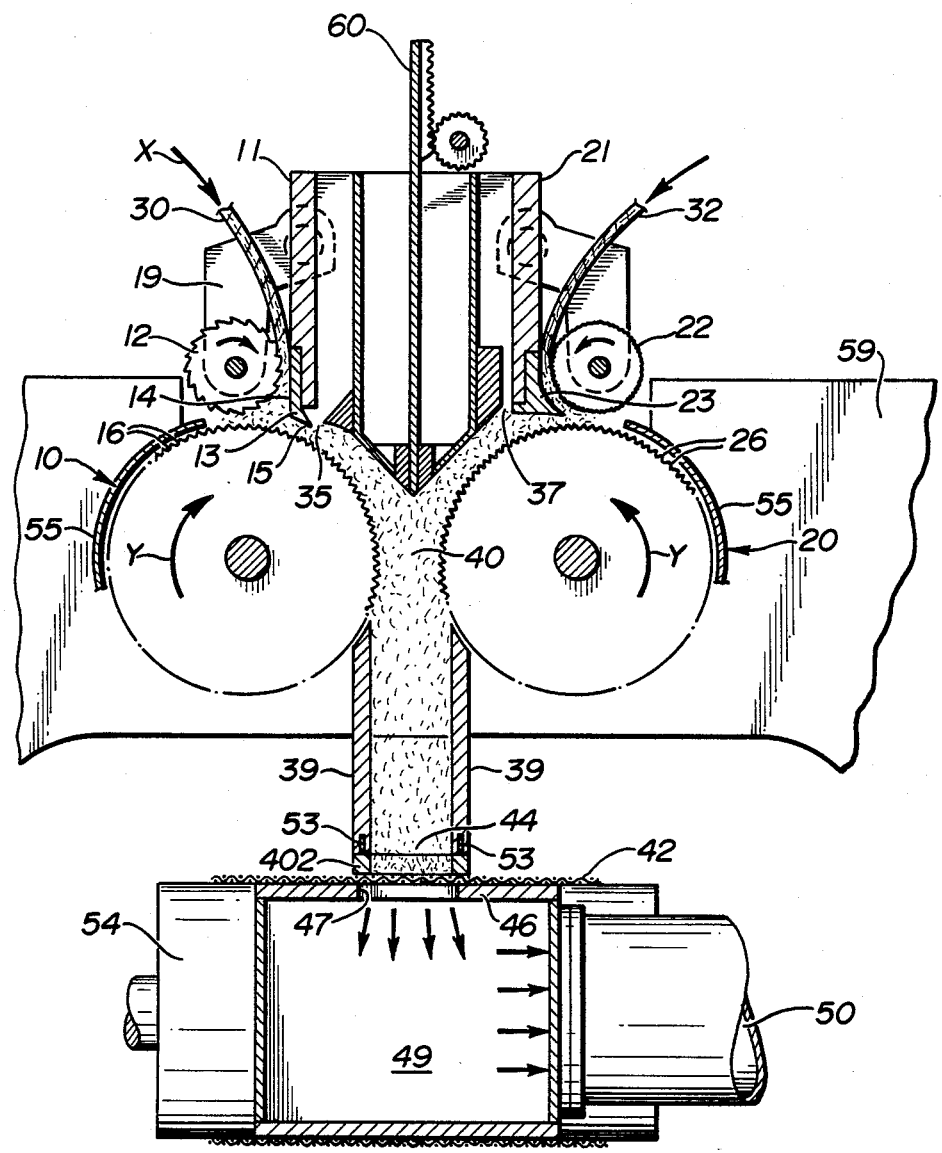
FIG. 2 is a more detailed cross-sectional view of an apparatus according to the invention.

FIGS. 1 and 2 show perspective schematic and cross-sectional views of the main components of an apparatus according to the invention. The invention is adapted to combine various fibers, e.g. short and long, into a nonwoven structure in a pocket or mold so as to form a product structure having variable horizontal and vertical cross-sectional compositions. Principally the apparatus comprises two lickerins 10, 20 operating in parallel. One lickerin 10 is adapted to individualize short fibers and the other lickerin 20 individualizes long fibers. The individualization of the fibers, but not formation of the structure, is generally performed according to commonly owned U.S. Pat. No. 3,740,797 to Farrington, the details of which are incorporated herein by reference.

Referring first to the short fibers, shown on the left, wood pulp A (FIG. 1) in the form of a pulpboard 30, is directed between a plate 11 (FIG. 2) and a wire wound feed roll 12. The plate 11 has a nose bar 13 on its lower part, which provides an anvil for the pulpboard 30 during individualization of the short fibers. The fibers are individualized by the rotating lickerin 10 disposed below the feed roll 12 and operatively adjacent to the nose bar 13. The nose bar 13 assists in directing the pulpboard 30 along a path defined by the plate 11, the feed roll 12, the lickerin 10, the nose bar 13 itself, and an inclined face 15 adjacent to the lickerin 10. These elements form a fiberizing station where the fibrous material, i.e., pulpboard 30, is converted into individual fibers. The inclined face 15 is spaced a short distance from the teeth 16 of the lickerin 10 and the pulpboard 30 is individualized into fibers by the teeth 16 of lickerin 10 acting on pulpboard 30 as it is brought into contact with the teeth 16 by the nose bar 13.

Typical short fibers include wood pulp fibers from various types of wood, cotton linters, asbestos fibers, glass fibers, and the like. Wood pulp fibers are the most frequently used, due to their low cost and ready availability. Pulp fibers are commercially available in the form of pulp boards of varying sizes and thicknesses.

For short fibers, the nose bar 13 may have a relatively flat sidewall 14 (FIG. 2). The feed roll 12 is eccentrically mounted to permit adjustment relative to side wall 14 and nose bar 13, as shown for example in FIG. 2 by bracket 19. The bracket 19 and feed roll 12 are resiliently biased to direct the pulpboard 30 against the nose bar 13 by known means, and drive the pulpboard into engagement with the teeth 16 of lickerin 10. This design permits the use of pulpboards of varying thicknesses.

Feed roll 12 is supported on a shaft and is rotated by conventional motor means (not shown). The feed roll 12 is rotated at a speed determined by the rate at which the pulpboard 30 is to be fed to the lickerin 10. This rate determines the amount of pulp fibers deposited to form the structure in a unit of time. The pulpboard 30 is fed to the feed roll 12 in the direction shown by the arrow in FIG. 1.

The lickerin 10 is likewise supported on a shaft and is rotated at a predetermined speed by a conventional motor (not shown), adapted to rapidly and reliably fray and comb the pulpboard 30 by engagement with the teeth 16 until individual fibers are liberated from the pulpboard. Short fibers individualized by lickerin 10 are carried to a mixing zone 40. Speeds in the neighborhood of 6000 rpm have been found suitable for this purpose. The teeth 16 are chosen to have an optimum profile for he chosen short fiber material represented by pulpboard 30.

Long fibers are individualized in much the same manner as the short fibers, as shown on the right side of FIGS. 1 and 2. Typical long fibers include synthetic fibers, such as cellulose acetate, vinyl chloride-vinyl acetate and viscose staple rayon fibers, and natural fibers, such as cotton, wool or silk. Long fibers, such as rayon, are commercially available in bales, with varying fiber lengths.

A source of long fibers is provided, usually in the form of a carded batt 32, as when rayon is used as the fiber source. Batt 32 is introduced to lickerin 20 via a second wire wound feed roll 22 acting in cooperation with a plate 21 and a nose bar 23. However, the nose bar 23 (FIG. 2), adapted for use with long fiber sources, differs from the nose bar 13 used with pulp. Since rayon and other long fiber sources lack the physical integrity of pulpboard, the batt 32 must be more positively restrained and directed into engagement with the lickerin 20. As shown in FIG. 2, the nose bar 23 is curved to essentially conform to the adjacent surface of the second feed roll 22. In this manner, the fibers in the rayon source are maintained in position with respect to the second feed roll 22 until they are delivered to the teeth 26 of lickerin 20.

The lickerin 20 is rotated at speeds such that the teeth 26 can comb long fibers from the batt 32 without degrading or damaging the long fibers. Speeds in the neighborhood of 3000 rpm have been found suitable for this purpose. The teeth 26 of lickerin 20 are generally shorter than the teeth 16 of lickerin 10, and have a smaller pitch.

A support structure or frame and drive means are, of course, provided for the various elements of the invention, as shown generally in the figures. Additionally, the lickerins, nose bars, feed rolls, etc. can be adjusted with respect to each other in order to achieve optimal results.

The long and short fibers may be individualized simultaneously or sequentially, and as shown in FIG. 1 there may be more that one type of each fiber (i.e., short fiber pulpboards A, B and long fiber batts C, D) distributed over portions of each lickerin. The lickerins 10, 20 are rotated toward each other, as shown by the arrows in FIGS. 1 and 2. The fiber sources, their distribution, and the speed and relative proportions at which they are individualized are chosen in order to produce the desired structure and combination of fibers.

The doffing of the individualized fibers from the lickerins, and the transmission of the fibers through the mixing zone 40 to a condensing zone 44 is assisted by air streams. As shown in FIG. 2, high velocity air can be drawn by suction created by a high vacuum chamber 49. This vacuum is formed by a fan driven by a motor (not shown) and drawn through duct 50 (FIG. 1). As a result air is drawn past the lickerins 10, 20 and the nose bars 13, 23, through the mixing zone 40, pocket molds 402 and the condensing screen 42. The fibers are entrained in the respective air streams and impelled to move rapidly and reliably from the lickerins 10, 20 toward each other in the mixing zone, and to pass through the mixing zone to the condensing zone, where they form the pads 45 in pockets 402.

According to the invention, the condensing zone 44 is defined within a space below and proximate to the mixing zone 40, just above the condensing screen 42, and between duct plates 39. The length of the condensing zone 44 corresponds to the length of the lickerins 10, 20. Thus, the condensing zone 44, according to the invention, is in the form of a long narrow trough adapted to receive individualized fibers from above.

The vacuum chamber 49 has the endless conveyor or condensing mesh screen 42 wrapped about it. The suction force from chamber 49 is applied to the condensing zone 44 through the mesh screen 42, for which a suitable aperture 47 is provided (FIG. 2) in the top of chamber 49. Alternatively, the pockets may have individual bottom screens 450, in which case mesh screens 42 can be replaced with a simple means for conveying the pockets through the condensing zone. The suction force may then extend through the bottom screen 450 of the pockets 402 (FIGS. 4 and 5), and out of the top of the pocket to the condensing zone.

The aperture in the vacuum chamber generally corresponds to the cross section of the space defined by the width of the pocket. The conveyor screen 42 is positioned to travel below and in communication with the condensing zone 44, in a direction that is parallel to the axes of rotation of the parallel lickerins 10, 20.

The condenser screen 42 is guided over conveyor rollers 52, 54, such that, it may pass about the high vacuum chamber 49. One or both of the rollers 52, 54 are driven so as to move screen 42 at a controlled rate.

The screen 42 may communicate with other conveyors, thereby delivering the pads 45 in the pocket molds for further processing as desired. Such processing may include bonding, as described for example in Lovgren, U.S. Pat. No. 3,772,739, shape-forming procedures, and final finishing of the web product.

In order to seal off the condensing zone 44, and to maximize the efficiency of the suction fan, duct plates 39 are extended downward toward the screen 42 and terminate above the top surface of the pocket. The duct plates 39 may additionally be provided with floating seals 53 (FIG. 2), which are biased into contact with the top surfaces of the pockets by a spring located behind the floating seals in a recess in duct wall 39. Lickerin covers 55 may also extend about the outer periphery of the lickerins and engage plates 39.

Figure 3:
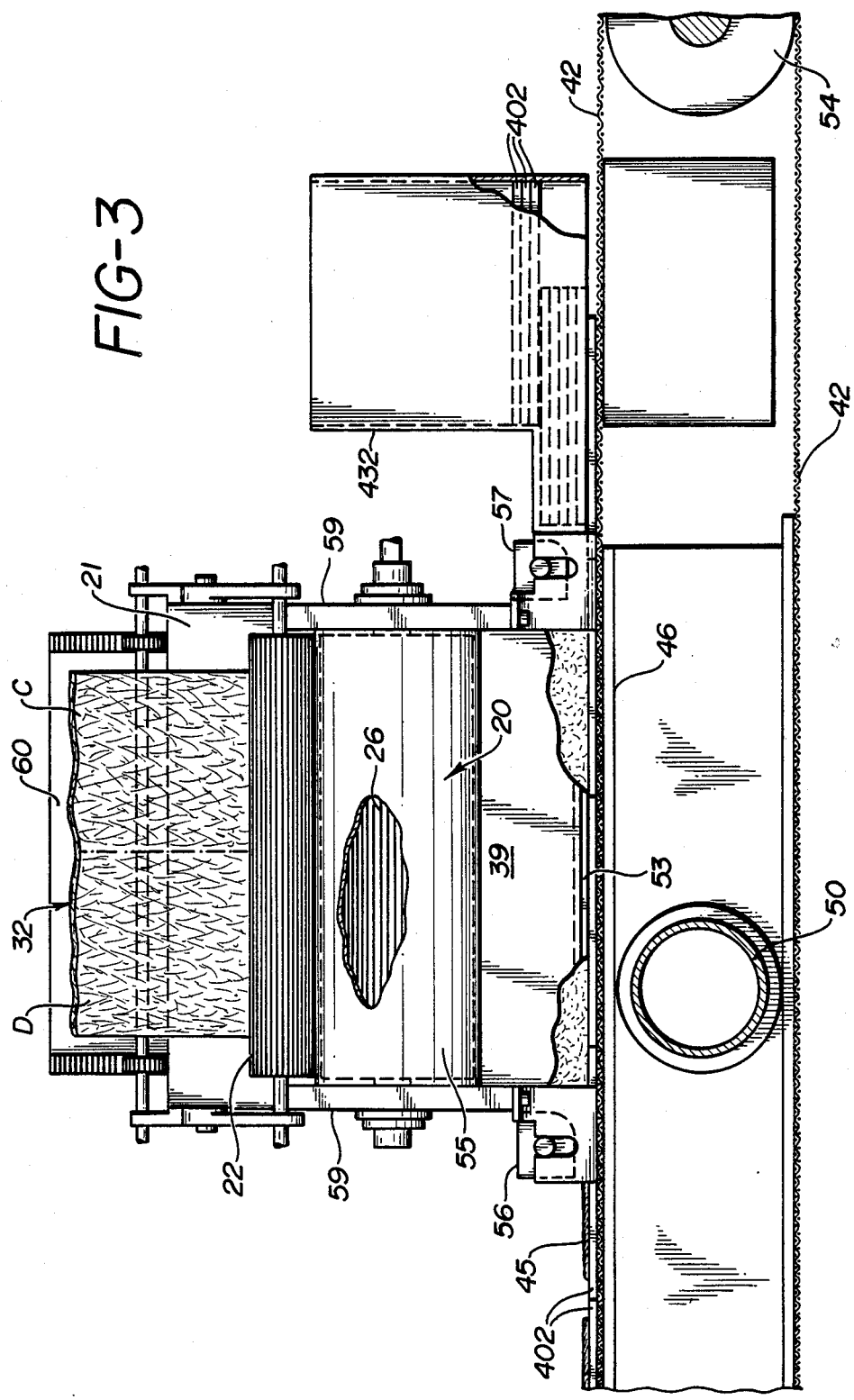
FIG. 3 is a side view of the apparatus of FIG. 2.

At the places where the pockets 402 enter and leave the condensing zone 44, sliding seals 57, 56, respectively, are provided on duct plates 59 (FIG. 3). The seals 56, 57 are disposed between the parallel edges of duct plates 39 and are free to float on the surface of the screen or pockets to accommodate movement of the screen and the pockets. When the pockets exit the condensing zone 44, they pass beneath seal 56. Besides maintaining the vacuum, the duct plates 39 serve to guide the fibers to the condensing zone 44 and, together with the duct plates 59, the floating seals 53, 56, 57, they improve the efficiency of the suction air flow.

Figure 8:
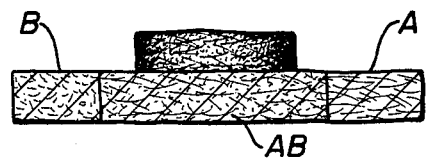
FIGS. 8-10 illustrate cross-sections of exemplary nonwoven fiber pads made with apparatus according to the present invention.
Figure 9:
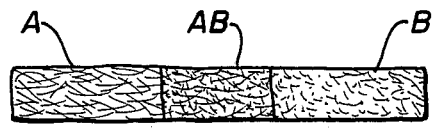
Figure 10:
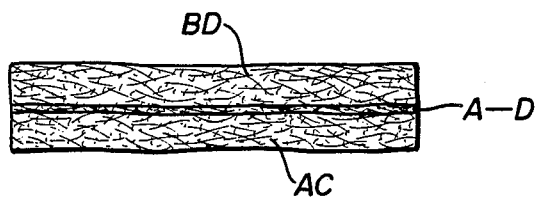

When the molds 402 are within the condensing zone 44, they are each in sealable contact with their serially adjacent molds in the machine direction, and are in sealable contact with the sealing assembly at the sides, so that the only available path for air-entrained fibers leads them into the molds 402. In this manner, a series of individual web structures is formed, each having a discrete contour defined by the shape of the mold 402. Exemplary products made according to this method and apparatus are shown in FIGS. 8–10.

The molds 402 may be permanently affixed to the conveyor screen 42, which is in the form of a continuous belt or chain, such that they continuously circulate through the condensing zone 44, with the end product removed from the molds 402 at a collection point downstream of zone 44.

In the alternative, the molds 402 can be fed from a cartridge-type assembly 430 (FIGS. 1 and 2), so that a series of unconnected molds 402 pass through the condensing zone 44 and are thereafter available for further processing prior to removal of the web product. As shown, the cartridge assembly 430 is a vertical rectangular structure, whose top is open to receive a stack of molds 402. The lower end of the side walls, except for wall 432 adjacent the condensing zone 44, are in sealing engagement with the condensing screen 42. At the base of wall 432 there is an opening 434 that is slightly larger than the cross section of one of the molds 402.

Since the conveyor screen 42 is moving, it makes friction contact with the lowest of the stack of molds in assembly 430 and drives it forward (to the left in FIG. 3) into the condensing zone beneath the lickerins 10, 20. Seal 57 is provided at the entrance of the molds to the condensing zone to maintain the vacuum. When this seal is used, the cartridge assembly 430 need not be immediately adjacent the condenser. Instead it can be at any convenient location along the conveyor, up stream from the condenser.

In order to improve the operation of feeding the pocket molds 402 into the condenser zone, the screen and the bottom of the molds may be coated with high friction material. Also small hooks may be spaced along the conveyor screen to engage the lowest mold and drag it into the condenser.

Figure 4:
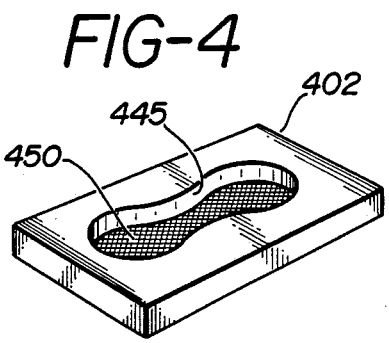
FIGS. 4 and 5 illustrate perspective views of single and double pocket molds.
Figure 5:
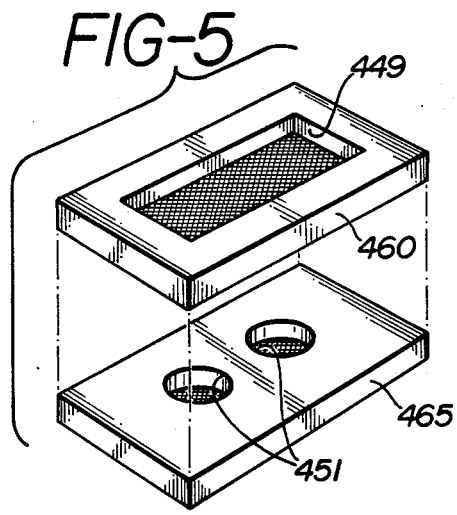
Figure 6:
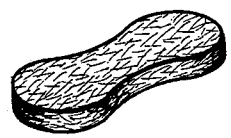
FIGS. 6 and 7 are perspective views of nonwoven web pads made according to the present invention.

The device according to the invention may also be provided with a retractable one piece or multiple-section baffle 60 disposed within a plane passing perpendicularly between the lickerins 10, 20 and intersecting the mixing zone 40. Although the baffle can be placed so that a downward leading edge falls at any predetermined point at or above the moving condenser screen 42, three distinct qualitative positions can be defined. When the baffle 60 or a part of the baffle is in the up or fully retracted position, its leading edge is removed from any functional contact with the fiber streams leaving the lickerins. When the baffle 60 or a part thereof is fully down, its downward leading edge is at or above the screen 42 at a predetermined position within the mixing zone 40 where it completely intercepts the fiber streams. Finally, the baffle 60 or one of the segments can be positioned so that its downward leading edge corresponds to a predetermined blend point within the mixing zone 40 where it partially blocks the fiber streams. A wide variety of composite structures, heretofore unknown, can be generated by the invention by varying the positions of or portions of the baffle 60 and by feeding one or more materials via each of the feed rolls 12, 22 adjacent these baffle portions. FIGS. 8–10 illustrate exemplary composite structures according to the invention, and as described according to the following examples. FIGS. 4–6 illustrate the shape of molds that are used to make products.

The pocket molds 402 delivered to the condensing zone 44 may be of the type shown in FIG. 4. This mold is generally rectangular in outer shape and may be made of any convenient material, i.e. wood, plastic, metal, etc. A recess 445, having the shape of the desired final or intermediate product, is formed completely through the mold. The bottom of the mold, however, may be closed with a screen mesh 450. As a result the vacuum force can be directed through the mold, but the fibers entrained in the air streams caused by the vacuum force are intercepted by the screen 450. The fibers collect in the recess 445 as the mold moves through the condensing zone. These fibers form a shaped structure of entangled fibers. In particular the "8" shaped mold of FIG. 4 results in a pad of fibers, which after further processing, is useful as a formfitted feminine sanitary napkin.

Figure 7:
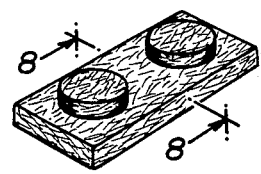

Other cavity shapes can be used to create other threedimensional pad shapes. The upper mold 460 of FIG. 5 has a rectangular recess 449 and would create a rectangular pad. The lower mold 465 in FIG. 5 has circular recesses 451 that produce two circular disk pads. If desired, molds may be stacked one above the other; so long as the upper mold cavity overlays and is larger than the cavity in the lower mold. Further, in stacking the molds, the screen 450 for the upper mold must be removed so that the fibers in the upper mold are linked with those in the lower mold. In FIG. 7 there is shown a product made by stacking molds 460 and 465, forming a web in them and turning the resulting pad upside down to eject it from the molds.

It will be understood by skilled practitioners that these examples represent only a few of the many new structures according to the invention. Moreover, it will be evident from the examples that, because of the transverse discharge of the forming web and the placement of the pocket molds, a uniformly blended web can not be obtained in the same manner as in known devices, such as the Farrington method and apparatus, of the previously identified Farrington patent. On the contrary, the transverse pocket webber according to the invention tends to deposit the fibers into a three dimensional web structure according to unique zone-forming patterns. These patterns can be manipulated to produce new and useful composite structures.

EXAMPLE 1

Two different fiber materials 30, 32 in the form of short and long fibers, respectively, were delivered to the feed rolls 12, 22 respectively, with each different fiber source being coextensive with one of the lickerins 10, 20. When the baffle 60 is in the up position, a composite web having three lateral zones is formed in the pocket molds, each running in the machine direction. The mold may be a stacked version of molds 460, 465 to form a product shaped as in FIG. 7. A schematic cross-sectional view of this product along line 8—8 of FIG. 7 is shown in FIG. 8. The zone-like composite structure is a consequence of the trajectories of the fibers doffed from the lickerins, passed through the mixing zone 40 and then formed into a transverse web in the mold while the mold is within the condensing zone 44.

When the baffle 60 is up, it does not alter the dilute fiber air stream trajectories as they pass through the mixing zone 40 to the condensing zone 44. The fiber air streams and their entrained fibers retain a component of motion tending to throw them away from their respective lickerin and toward the web on the side of the opposing lickerin. As a result, the fibers tend to pass each other within the mixing zone 40 because the streams are so dilute that there is little tendency for fiber collisions. Thus, the fibers are predominantly deposited toward opposite sides of the mold in the condensing zone 44. As shown in FIG. 8, short fibers A originating from a left-hand lickerin tend to form a narrow right-hand fiber zone A containing predominantly fibers A. The long fibers B originating from the right-hand lickerin tend to form a narrow left-hand zone B containing predominantly fibers B. Between the fiber zones A and B is a wider transition zone containing a blend of fibers A+B. At the boundaries of the zones the fibers are entangled so that the web is formed in one piece.

EXAMPLE 2

The fiber sources of Example 1 are used, but the baffle 60 is positioned at a blend point within the mixing zone 40 in order to influence the trajectories of the individualized fibers prior to final deposition as a web in the mold. The individualized fibers passing through the mixing zone 40 and on to the condensing zone 44 from each lickerin fall within a range or angle of trajectories, in the manner of a spray exiting a nozzle. The baffle 60, when positioned at the predetermined blend point, intersects at least part of the trajectory angle, causing some of the fibers entrained in the air flow within that part of the angle to bounce off the baffle 60 back toward its own originating side of the condensing zone 44.

With the blend point chosen so that approximately equal volumes of fiber from each lickerin are redirected by the baffle 60 as are permitted to pass under the baffle 60 without interruption, a uniformly blended web of short and long fibers A+B is obtained. The blend point can, of course, be chosen to provide a wide variety of fiber deposition patterns and resulting nonwoven web structures.

EXAMPLE 3

In yet another embodiment, the baffle 60 is placed in a down position, approximately 2 inches above the screen 42. The two different fiber sources A, B of Example 2 are used such that each fiber is supplied over an operative length of one of the parallel lickerins 10, 20. In this case, substantially all of the fiber trajectories are interrupted by the baffle, tending to throw the fibers back toward their originating side of the condensing zone 44. The result is a web similar to the web in Example 1, but with the fiber zones A and B in reverse order, and a narrower transition zone A+B as shown in FIG. 9.

It should be appreciated that regardless of the position of the baffle, there will be some distribution of both long and short fibers across the web due to the turbulent air flow. Thus the zone representations in FIGS. 8 and 9 merely show the predominate fibers in each. The proportion of fibers in each zone may also be regulated by the rate at which the fiber sources 30, 32 are fed to the lickerins. A fiber fed at a faster rate will produce a greater concentration of that product in the web, although it will be distributed across the web in a manner determined by the baffle position.

EXAMPLE 4

Each lickerin 10, 20 need not be supplied entirely with one fiber source, provided that all of the fibers supplied to each lickerin conform to the fiber type (short or long) for which the lickerin is adapted. Thus, for example, four fiber sources A–D are equally distributed among the two lickerins, each such source covering half of its respective lickerin. Moreover, the fibers may be fed into the lickerin by feed rollers rotating at different speeds. FIG. 1 also illustrates this embodiment. Two different pulpboards 30, 31 for producing short fibers A, B are fed to lickerin 10 and two different textile fibers batts 32, 33 for producing long fibers C, D are fed to lickerin 20. The fiber combination A, C toward the entrance end of the apparatus produce a lower layer of the web while the fiber combination B, D toward the exit end of the apparatus produce an upper layer.

The multiple fiber supplies A-D of FIG. 1 are fed to the apparatus with the baffle in a blend point position to promote uniform mixing and deposition of fibers. The two rearward fiber sources A and C in the machine direction supply their fibers to the mold first. As this portion of the mold moves toward the exit it passes below the transition between sources AC and BD, and a transition layer having a uniform mixture of all four fibers is laid down on top of the lower layer. As the screen portion moves under the region of the lickerins which are fed fibers B, D, these are deposited as an upper uniformly blended layer of B and D in order to form the product whose cross section is shown in FIG. 10. If the baffle 60 is made in a plurality of sections, these sections can be individually set to vary the blend ratio in different layers of the product. For example, the two layers shown in FIG. 10 can be in the form shown in FIG. 8 and 9.

OTHER VARIATIONS

A product in which a middle layer is surrounded by other layers can be very advantageous as a absorber, e.g. a diaper or sanitary napkin. With such a product the inner fiber blends are selected to be high absorbency fibers. For example this layer may be made predominately of pulp or super absorbing fibers. The outer fibers are selected for their wicking property, i.e. the ability to move liquid. For example, rayon fibers have good wicking properties. With such a product the moisture is directed away from the user's skin and clothing by the wicking fibers and is retained in the center of the product by the high absorbency fibers.

If the feeding of the pulp or high absorbency fibers is intermittent, patches of this material will be buried in the pad formed.

Various other products can be made in segments by starting and stopping the condenser screen and by starting and stopping or sequentially feeding the various fiber materials A,B,C,& D to the lickerins. Also, fibers may be included which provide properties to the product other than moisture handling. For example a fibrous material with great resiliency may be used to give a product, e.g. a napkin, a springy characteristic that makes it feel like a plush material.

While the present invention has been particularly shown and described with reference to preferred embodiments thereof, it will be understood by those skilled in the art that various changes in form and details may be made therein without departing from the spirit and scope of the invention.

What is claimed is:

1. A pad product forming apparatus comprising:
    first feed means for feeding a fibrous material to a first fiberizing station at a first location;
    second feed means for feeding a fibrous material to a second fiberizing station at a second location;
    means defining a mixing zone between said fiberizing stations;
    first and second lickerins mounted for rotation toward each other about respective parallel axes, a portion of the outer periphery of said first and second lickerins being adjacent to said first and second feeding means, respectively, at the first and second fiberizing stations, respectively; said first and second lickerins being engageable with the fibrous materials feed to the respective fiberizing stations so as to open the materials and produce individualized fibers moving in first and second streams, respectively, in trajectories toward each other and said mixing zone;
    conveyor means that is at least partially permeable to air and moves parallel to the lickerin axes, said conveyor means being located beyond said mixing zone;
    condensing zone between the conveyor means and the mixing zone, said conveyor means entering said condensing zone at an entrance end and leaving at an exit end of said condensing zone;
    at least one mold, separate from said conveyor means and having a predetermined pocket shape corresponding to the desired individual shape of the pad, said mold being adapted to receive therein fibers in the air stream from the mixing zone and being introduced to the condensing zone by said conveyor means;
    a foraminous surface in contact with a lower surface of said mold and being in at least partial communication with an air permeable portion of the conveyor; and
    a vacuum means in selective communication with said condensing zone through the air permeable portions of said conveyor and the foraminous surface while said mold is passing through said condensing zone, said vacuum means tending to draw air-entrained fibers into said molds for condensation therein on the foraminous surface.

2. A pad forming apparatus as claimed in claim 1, wherein said conveyor means comprises a continuous foraminous belt that forms said foraminous surface and wherein said at least one mold is a series of molds immediately adjacent each other.

3. A pad forming apparatus as claimed in claim 1 wherein said foraminous surface is a part of said at least one mold.

4. A pad forming apparatus as claimed in claim 1, wherein said mold is a plurality of molds stacked vertically one above the other in a structure, said structure being located above the conveyor means upstream from the condensing zone along the conveyor, the bottom most mold being in contact with the conveyor such that it is drawn through an opening in a side wall of the structure along with the conveyor and into the condensing zone through said sealing means.

5. A pad forming apparatus as claimed in claim 1 further including means for separating the mold from the fibers. condensed therein at a separation point downstream of said condensing zone.

6. A method of forming a pad of fibers comprising the steps of:
    feeding a first source of fibrous material into engagement with a first lickerin;
    feeding a second source of fibrous material into engagement with a second lickerin arranged with its axis parallel to the axis of said first lickerin;

rotating said first and second lickerins toward each other about their axes such that the fibrous material is opened so as to form individual fibers;

doffing the fibers from the first and second lickerins in the form of two fiber streams directed toward each other and into a mixing zone;

conveying said fibers streams from the mixing zone to a condensing zone;

conveying said fibers into an individually shaped pad having a greater proportion of one of said fibers in a first portion of said pad than in a second portion of said pad within at least one mold, while conveying said mold through said condensing zone in a direction parallel to the axes of said lickerins; and providing said mold with a foraminous surface, separate from said mold, in contact with the mold's surface remote from the fiber streams so as to allow accumulation of fibers in the mold.

7. A method according to claim 6 further including the step of removing said web product from said mold.

8. A method according to claim 6, wherein said conveying and condensing steps additionally comprise entraining said fibers in a vacuum-induced air stream directed through the foraminous surface of said mold.

9. A pad product forming apparatus comprising:

first feed means for feeding a fibrous material to a first fiberizing station at a first location;

second feed means for feeding a fibrous material to a second fiberizing station at a second location;

means defining a mixing zone between said fiberizing stations;

first and second lickerins mounted for rotation toward each other about respective parallel axes, a portion of the outer periphery of said first and second lickerins being adjacent to said first and second feeding means, respectively, at the first and second fiberizing stations, respectively; said first and second lickerins being engageable with the fibrous materials feed to the respective fiberizing stations so as to open the materials and produce individualized fibers moving in first and second streams, respectively, in trajectories toward each other and said mixing zone;

conveyor means that is at least partially permeable to air and moves parallel to the lickerin axes, said conveyor means being located beyond said mixing zone;

condensing zone between the conveyor means and the mixing zone, said conveyor means entering said condensing zone at an entrance end and leaving at an exit end of said condensing zone;

at least one mold having a predetermined shape corresponding to the desired individual shape of the pad, said mold being adapted to receive fibers in the air stream from the mixing zone and being introduced to the condensing zone by said conveyor means;

a foraminous surface in contact with a lower surface of said mold and being in at least partial communication with an air permeable portion of the conveyor;

a vacuum means in selective communication with said condensing zone through the air permeable portions of said conveyor and the foraminous surface while said mold is passing through said condensing zone, said vacuum means tending to draw air-entrained fibers into said molds for condensation therein on the foraminous surface; and baffle means for controlling the flow of fibers in said first and second streams, said baffle extending into said mixing zone in a plane parallel to the axes of said lickerins and substantially perpendicular to said mold, ending at a distance from said mold which varies along a direction parallel to said axes.

10. A method of forming a pad of fibers comprising the steps of:

feeding a first source of fibrous material into engagement with a first lickerin;

feeding a second source of fibrous material into engagement with a second lickerin arranged with its axis parallel to the axis of said first lickerin;

rotating said first and second lickerins toward each other about their axes such that the fibrous material is opened so as to form individualized fibers;

doffing the fibers from the first and second lickerins in the form of two fiber streams directed toward each other and into a mixing zone;

conveying said fibers streams from the mixing zone to a condensing zone;

condensing said fibers into an individually shaped pad within at least one mold, while conveying said mold through said condensing zone in a direction parallel to the axes of said lickerins;

providing said mold with a foraminous surface, separate from the mold, in contact with the mold's surface remote from the fiber streams so as to allow accumulation of fibers in the mold; and baffling the fiber streams to vary the mixture of the fibers accumulating in the mold as the mold moves in the direction parallel to the lickerin axes.

* * * * *